US005853738A

United States Patent [19]
Istrate et al.

[11] Patent Number: 5,853,738
[45] Date of Patent: Dec. 29, 1998

[54] METHODS FOR TREATMENT OF HUMAN IMMUNODEFICIENCY VIRUS INFECTION WITH PSEUDOMONAS PHOSPHOAMINOLIPID EXTRACT

[75] Inventors: Nicolae Istrate, Lexington; Gita Muni, North Reading; Edgard Brauner, Brighton; Fazal Raheman, Burlington, all of Mass.

[73] Assignee: Dynagen, Inc., Cambridge, Mass.

[21] Appl. No.: 550,393

[22] Filed: Oct. 30, 1995

[51] Int. Cl.$^6$ .................. A61K 39/108; A61K 39/21; A61K 39/02
[52] U.S. Cl. ................ 424/260.1; 424/184; 424/187.1; 424/188.1; 424/234.1
[58] Field of Search .................. 424/92, 184.1, 424/260.1, 187.1, 188.1

[56] References Cited

U.S. PATENT DOCUMENTS 4,182,751  1/1980  Ayme ........................ 424/92

OTHER PUBLICATIONS

Olinescu, A; Hristescu, S; Salageanu, A; Manda, G; Neagu, M: In vivo and in vitro affect of Cantastim, an immunomodulatory agent extracted . . . Neoplasma: 38/1:pp. 119–128: 1991.

Negut E, G. Szegli, I Peligrad, C Matache, A. Olinescu, and A. Morx: Immunomodulation Activity of a Pseudomonas Aeruginosa Extract–Cantastim: Arch. Roum. Path. Exp. Microbial: T.44, No. 4 pp. 323–335: 1985.

M. Piatek, Jr. et al., "High Levels of HIV–1 in Plasma During All Stages of Infection Determined by Competitive PCR", *Science*, 1993, vol. 259, pp. 1749–1754.

David A. Katzenstein, M.D. et al., "The Relation of Virologic and Immunologic Markers to Clinical Outcomes After Nucleoside Therapy in HIV–Infected Adults with 200 to 500 CD4 Cells per Cubic Millimeter", *The New England Journal of Medicine*, 1996, vol. 335, No. 15, pp. 1091–1098.

Louis D. Saravolatz, M.D. et al., "Zidovudine Alone or in Combination with Didanosine or Zalcitabine in HIV–Infected Patients with the Acquired Immunodeficiency Syndrome or Fewer Than 200 CD4 Cells per Cubic Millimeter", *The New England Journal of Medicine*, 1996, vol. 335, No. 15, pp. 1099–1106.

Lawrence Corey, M.D. et al., "Therapy for Human Immunodeficiency Virus Infection–What Have We Learned?", *The New England Journal of Medicine*, 1996, ol. 335, No. 15, pp. 1142–1143.

Sudhir Gupta (edited by), "Immunology of HIV Infection", *Plenum Press*, 1996, 475–491.

Scott M. Hammer, M.D. et al., "A Trial Comparing Nucleoside Monotherapy with Combination Therapy in HIV–Infected Adults with CD4 Cell Counts from 200 to 500 per Cubic Millimeter", *The New England Journal of Medicine*, 1996, vol. 335, No. 15, pp. 1081–1090.

Likhite, V., "Experimental Cancer Immunotherapy: Comparison of Tumor Rejection . . . Carynobacterium parvum", *Exp. Cancer Immunother.*, (1976), 985–989.

Antony, V., et al., "Bacillus Calmette — Guerin–stimulated Neutrophils Release Chemotaxins for Monocytes in Rabbit Pleural Spaces and in Vitro", *J. Clin. Invest.*, (1985), 76:1514–1521.

Jackson, A., et al., "Inductions of ICAM 1 expression on bladder tumours by BCG immunotherapy", *J. Clin. Invest.*, (1994), 76:1514–1521.

Danforth, J., et al., "Microphage Inflammatory protein–1–alpha expression . . . lipoteichoic acid", *Clin. Immunopath.*, (1995), 74:1, Abstract.

Usami, H., et al., "Antitumour effects of streptococcal lipoteichoic acids on Meth A fribrosarcoma", *Br. J. Cancer*, (1988), 57:70–73.

Ohshima, Y., et al., "Activation of Mononuclear Immune Cells in Response to Staphylococcal Lipoteichoic Acid", *Zbl. Bakt.*, (1991), 275:374–381.

Keller, R., et al., "Macrophage Response to Bacteria: Induction of Marked Secretory and Cellular Activities by Lipoteichoic Acids", *Infect. & Immun.*, (1992), 60:9:3664–3672.

Kusunoki, T., et al., "Molecules from *Staphylococcus aureus* that Bind CD14 and Stimulate Innate Immune Responses", *J. Exp. Med.*, (1995), 182:1673–1682.

Olinescu, A., et al., "Normal Immune Functions Consequent to Cantastim Therapy in a Case of Chronic Lymphatic Leukemia T CLLT", Rev IG Bacteriol Virusol Parazitol Epidemiol Pneumoftiziol Seb Bacteriol Virusol Parazitol Epidemiol, (1988) 33:3:281–288.

*Primary Examiner*—Lynette F. Smith
*Assistant Examiner*—Brett Nelson
*Attorney, Agent, or Firm*—Wolf, Greenfield & Sacks, P.C.

[57] ABSTRACT

The present invention is directed to a method of treating individuals infected with HIV or at risk of being infected with HIV. The method comprises the step of administering to an individual infected with HIV or at risk of being infected with HIV, an effective amount of a phosphoaminolipid extract derived from bacteria. The phosphoaminolipid extract exhibits an immunomodulating effect in humans, promoting a stabilization or improvement in immune system function.

16 Claims, 4 Drawing Sheets

1

METHODS FOR TREATMENT OF HUMAN IMMUNODEFICIENCY VIRUS INFECTION WITH PSEUDOMONAS PHOSPHOAMINOLIPID EXTRACT

FIELD OF INVENTION

This invention pertains to the field of immunopharmacology and, in particular, the use of a phosphoaminolipid extract derived from bacteria of the genus of Pseudomonas to modulate the immune defense mechanisms of HIV infected patients.

BACKGROUND

Acquired Immunodeficiency Syndrome (AIDS) is a disease of the human immune system. AIDS is caused by infection with Human Immunodeficiency Virus (HIV). Individuals infected with HIV exhibit abnormally low immune function and wasting. The compromised immune function renders the subject highly vulnerable to various opportunistic infections and cancers. Many of the opportunistic infections and cancers in HIV infected individuals are rare in immunocompetent individuals. However, in subjects with HIV infections, these secondary infections and cancers are common and can be life threatening. Wasting is an unintentional reduction in body weight greater than ten percent.

Since the discovery of HIV in 1983, significant efforts have been made toward the discovery and development of anti-HIV drugs. Despite these efforts, clinical therapy remains largely palliative. Most of the anti-HIV drugs, in various phases of development or already FDA approved, target one or more steps in the life cycle of HIV.

The immunological improvement induced by available anti-HIV therapies in patients with AIDS is incomplete and transient. Drugs used in treatments tend to have low therapeutic indices. The drugs exhibit toxicity. The virus has exhibited a striking ability to adapt to drugs and quickly develop drug resistance.

Attempts to manipulate the immune system of individuals who have HIV infection and those individuals at high risk to acquire HIV infection focus on vaccines. Despite a substantial effort, attempts to develop a vaccine have been frustrated by the ability of the virus to directly attack the immune system and its ability to overcome through mutation, vaccines with single or multiple number antigenic components.

Immunostimulants have been used in HIV infection therapy in order to improve or restore some deteriorated components of the immune system, primarily cell-mediated-immunity. A number of immunostimulants used or likely to be used in different preclinical or clinical studies of HIV infection therapies comprise clinical stage, acute (primary) infection, asymptomatic, early symptomatic and AIDS. However, the effectiveness of such immunostimulants has not been clearly established.

In an effort to evaluate drugs and therapies as quickly as possible, researchers have relied on endpoints which may, but not necessarily, reflect some benefit to the patient. These end points or "surrogate-markers" comprise only some immune parameters, such as the number of CD4+ lymphocytes at a particular point in time, or the level of circulating HIV. Several existing and proposed therapies tend to demonstrate an ability to affect endpoints or surrogate markers. However, none of the therapies demonstrate a significant clinical benefit in HIV patients in keeping them free or nearly free of opportunistic infections, improving their quality of life, and delaying the progression of the disease.

At present, none of the therapies are well tolerated. The therapies generally have significant side effects. The therapies are also expensive. So expensive, that even in industrial countries, many individuals infected with HIV cannot afford treatment. In less developed countries, most individuals infected with HIV do not receive treatment.

There presently exists a need for a treatment of HIV which restores immune function with resulting clinical benefits. Such therapies should prevent loss of body weight, and even promote weight gain. Such therapies should improve the response to the treatment of existing opportunistic infections, prevent the recurrence of the treated opportunistic infection and keep free of or reduce the number of opportunistic infection experienced.

It is highly desirable to extend the asymptomatic period of HIV patients, and prevent or delay the progression of HIV infection to AIDS. Even therapies which extend the asymptomatic period of HIV patients and the progression of HIV infection to AIDS for periods of six months would have a significant benefit. Such a limited period would reduce health costs, which can be expensive, and maintain the productivity of the individual.

A preferred therapy for HIV infection would be safely administered with few side effects. A preferred therapy would be administered with minimal disruption of the individual's daily routine. A preferred therapy would be more affordable than present therapies.

SUMMARY OF THE INVENTION

The present invention is directed to a method of treating individuals infected with HIV or at risk of being infected with HIV. The method comprises the step of administering to an individual infected with HIV or at risk of being infected with HIV, an effective amount of a phosphoaminolipid extract derived from bacteria of the genus Pseudomonas. The phosphoaminolipid extract exhibits an immunomodulating effect in humans, promoting a stabilization or increase in immune system function.

The phosphoaminolipid extract derived from bacteria of the genus Pseudomonas is preferably derived from at least one of the species consisting of aeruginosa, putida, fluorescens, chlororaphis, aureofaciens, syringae, cichorii, stutzeri, mendocina, alcaligenes, pseudoalcaligenes, pseudomallei, mallei, caryophylli, cepacia, marginata, lemoignei, testosteroni, acidovorans, delafieldii, solanacearum, facilis, saccharophila, ruhlandii, flava, palleronii, maltophilia, vesicularis and diminuta.

A preferred bacteria is *Pseudomonas aeruginosa*. A preferred *Pseudomonas aeruginosa* strain is strain 4922. A preferred phosphoaminolipid extract derived from *Pseudomonas aeruginosa* is sold under the trademark "CANTASTIM™". This product is characterized as 88–92% phospholipid and aminolipid, 3–5% sugars and 5–7% proteins. Biological activity is believed related to the lipid components.

The phospholipid extract may be partially purified to remove components which do not participate in the immunomodulating effect. The phospholipid extract may be made through synthetic or recombinant means.

As used herein, an "effective amount of a phospholipid extract" refers to an amount of such extract which when administered orally, subcutaneously, intramuscularly, intravenously, by aerosol to pulmonary tissues, intradermally, or rectally, produces an immune response in the individual. Such response is manifested by a stabilization or improvement in immune system function. Immune system function, in HIV infected individuals, is usually described with respect to CD4 cell count and circulating HIV levels found in blood samples.

An effective amount of phosphoaminolipid extract derived from Pseudomonas aeruginosa comprises 0.1–10.0 mg. Preferably, the amount is in the range of 0.5–1.0 mg. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered weekly for up to fifty-two weeks; more preferably, for up to thirty-two weeks, and even more preferably, for four to fourteen weeks.

Preferably, after a period of administration of the phosphoaminolipid extract, the therapy is discontinued for four to 52 weeks and restarted. Even more preferred, the therapy is restarted after eight to fourteen weeks.

A preferred manner of administration of the phosphoaminolipid extract is 0.5–1.0 mg, subcutaneously, weekly for four to eight weeks. This regimen is restarted after a break of four to eight weeks. This cycle of administration and breaks are repeated as necessary.

The effective amount, 0.5–1.0 mg of phosphoaminolipid extract, is usually administered in a solution suitable for subcutaneous administration. A typical solution for administration contains 0.5 to 1.0 mg extract/ml with suitable preservatives, buffers and salts.

Embodiments of the present invention provide many clinical benefits to individuals infected with HIV. The present invention prevents or delays immune function deterioration in asymptomatic individuals. Indeed, some individuals exhibit improved immune function.

Such individuals exhibit fewer opportunistic infections and improved responses to therapies for opportunistic infections. Such individuals exhibit stable weight or even weight gain. Individuals who receive treatment in accordance with the present invention exhibit fewer symptoms of polyclonal hyperactivity and autoimmune disease. These individuals perceive improvements in the quality of their life.

Embodiments of the present invention provide a cost effective therapy for HIV infection and AIDS. Indeed, the phosphoaminolipid of the present invention can be produced without sophisticated chemical synthesis. Thus, the present invention can be made widely available in industrial and non-industrial countries.

The phosphoaminolipid extract of the present method is well tolerated and can be used in combination with other therapies. Therefore, individuals are more apt to complete therapy and receive its benefits.

These and other benefits will be apparent to individuals skilled in the art, as described more fully in the Drawings and Detailed Description.

DETAILED DESCRIPTION OF THE INVENTION

Figure 1:
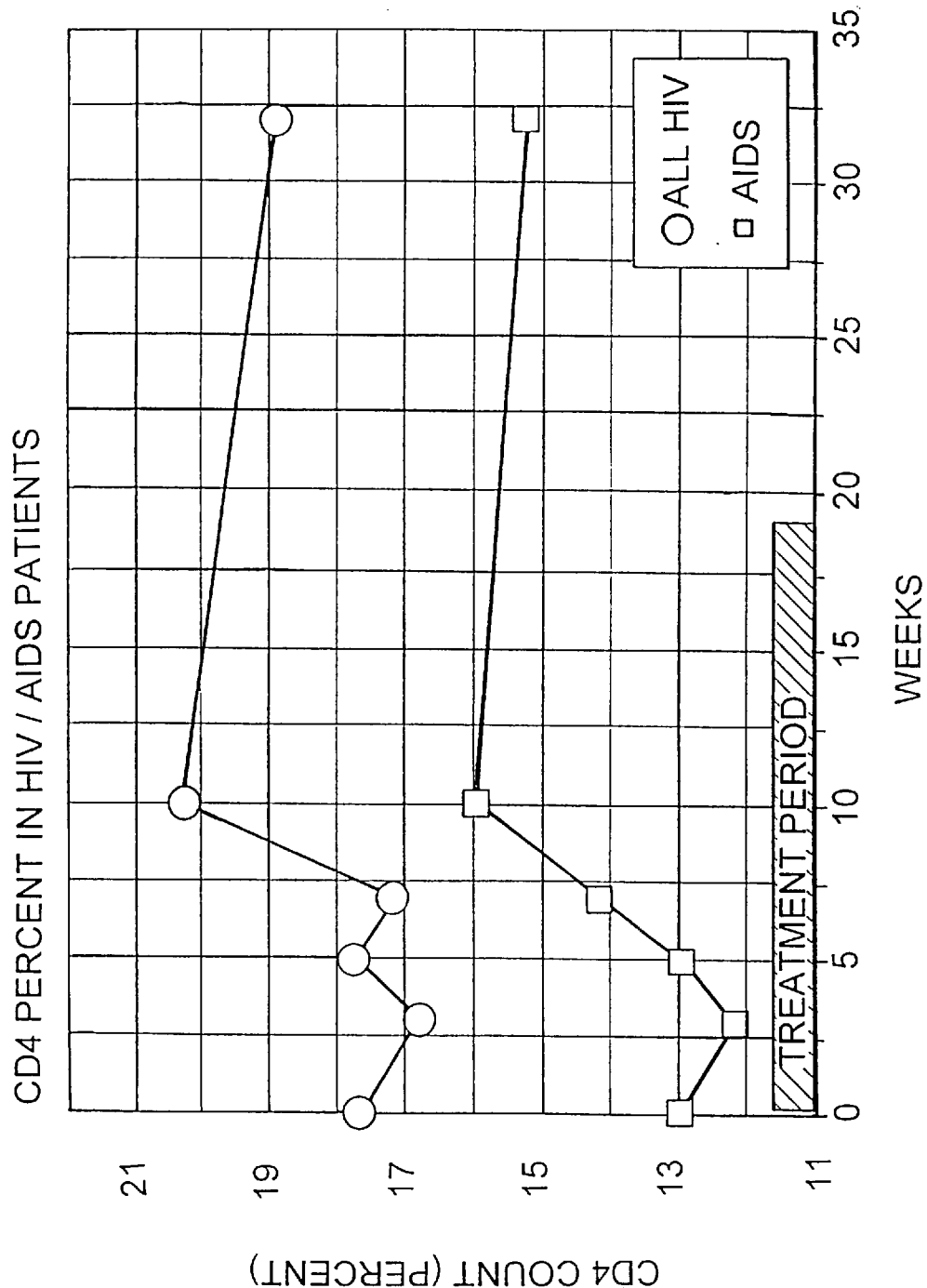
FIG. 1 graphically depicts CD4 percent in HIV/AIDS patients receiving therapy in accordance with the present invention.

The present invention will be described in detail as a method of treating individuals infected with HIV or at risk of being infected with HIV. As used herein, the term "individuals infected with HIV" includes those individuals who may be infected by HIV but do not test positive for anti-HIV antibodies on EIA tests or Western Blot procedures. For example, without limitation, individuals who may have been infected with HIV but have not developed anti-HIV antibodies due to the short period of time between the act of infection and the test for presence of antibodies.

As used herein, the term "at risk" refers to individuals who due to lifestyle or medical conditions have a high probability of becoming infected with HIV virus. For example, without limitation, individuals receiving blood transfusions, blood products, or receiving organ transplants may be at higher risk than the general population due to the potential of contaminated blood.

As used herein, the term "AIDS" refers to a status, as defined by the Center for Disease Control criteria. These criteria are any of the following two characteristics:
1. Infection with HIV and a CD4+ cell count below 200/mm$^3$ or a CD4+ cell count below 14%, with or without an opportunistic infection; or,
2. Infection with HIV and a CD4+ cell count greater than 200/mm$^3$ or CD+ cell count greater than 14% but who exhibit one or more of the following conditions:
   Candidiasis of bronchi, trachea or lungs
   Candidiasis, esophageal
   Cervical cancer, invasive
   Coccidioid mycosis, disseminated or extrapulmonary
   Cryptococcoses, extrapulmonary
   Cryptosporidiosis, chronic intestinal (>1 month's duration)
   Cytomegalovirus disease (other than liver, spleen or nodes)
   *Cytomegalus retinitis* (with loss of vision)
   Encephalopathy, HIV-related
   Herpes simplex: chronic ulcer(s) (>1 month's duration) or bronchitis, pneumonitis, or esophagitis
   Histoplasmosis, disseminated or extrapulmonary
   Isosoporiasis, chronic intestinal (>1 month's duration)
   Kaposi's sarcoma
   Lymphoma, immunoblastic (or equivalent term)
   Lymphoma, primary, or brain
   MAIS complex or *M. kansasii,* disseminated or extrapulmonary
   *M. tuberculosis,* any site (pulmonary or extrapulmonary)
   *Pneumocystis carinii* pneumonia
   Pneumonia, recurrent
   Progressive multifocal leukoencephalopathy
   *Salmonella septicemia,* recurrent
   Toxoplasmosis of brain
   Wasting syndrome due to HIV One embodiment of the present invention is a method of treating individuals infected with HIV or at risk of being infected with HIV. The method comprises the step of administering to an individual, infected with HIV or at risk for being infected with HIV, an effective amount of an immunomodulating phosphoaminolipid composition derived from bacteria of the genus Pseudomonas. The immunomodulating phosphoaminolipid composition promotes a stabilization or increase in immune system function.

The stabilization or increase in immune system function is manifested by any one or more immune parameters, comprising CD4 cell count, CD4+ percent, and HIV plasma load.

The phosphoaminolipid extract from bacteria of the genus Pseudomonas is preferably derived from at least one species consisting of aeruginosa, putida, fluorescens, chlororaphis, aureofaciens, syringae, cichorii, stutzeri, mendocina, alcaligenes, pseudoalcaligenes, pseudomallei, mallei, caryophylli, cepacia, marginata, lemoignei, testosteroni, acidovorans, delafieldii, solanacearum, facilis, saccharophila, ruhlandii, flava, palleronii, maltophilia, vesicularis and diminuta. A preferred species is aeruginosa.

A preferred *Pseudomonas aeruginosa* is strain 4922. A preferred phosphoaminolipid extract is sold under the trademark "CANTASTIM™". This extract is made by in accordance with the methods described in Marx, A., Petcovici, M.: "Immunochemical Studies on Purified Common Enterobacterial Antigen (Kunin)", *Zbl. Bakt. Hys.* 1 Hbt Orig., 233 1975 486.

In brief, *Pseudomonas aeruginosa* strain 4922 is grown in culture in suitable group media. The bacteria are pelleted by centrifugation at 3,000×g 30 minutes or in continuous flow centrifuge. 2,000 mL 95% ethanol is added to 200 g moist microbial mass. The suspended bacteria in ethanol are heated to 60° C. with constant mixing for 20 minutes then cooled to 20° C. The bacteria are spun down for 30 minutes at 13,000×g. The supernatant is transferred to a rotary evaporator and concentrated to a point at which it becomes viscous fluid (complete drying should be avoided). This viscous fluid is redissolved in 40 mL 85% ethanol. The soluble phase is decanted into a centrifuge tube and precipitated with 3 volumes of acetone. The whole mixture is spun down for 5 minutes at 6,000×g. The supernatant is discarded and the sediment is dissolved in 4 mLs distilled water. The aqueous solution is passed onto Sephodex C75 (column 25×350 mm). The Vo fraction (read at 275 m$\mu$) contained the product of interest. This fraction is concentrated to a final concentration of 3.5 mg/mL and is sterilized.

Chemical analysis of this product shows 88–92% phospholipids and aminolipids, 3–5% sugars and 5–7% proteins. Biological activity is due to lipid component. The sugar and protein components, apart from the lipid component, do not appear to exhibit immunomodulating properties.

An effective amount of phosphoaminolipid extract derived from *Pseudomonas aeruginosa* comprises 0.1–10.0 mg. Preferably, the amount is in the range of 0.5–1.0 mg. Preferably, the effective amount is administered more than once. Preferably, the effective amount is administered every day to every thirty days and, more preferably, every five to fifteen days. This regimen can be maintained for up to six months to one year, or even the life of a is subject. Preferably, the effective amount is administered weekly for up to fifty-two weeks; more preferably, for up to thirty-two weeks, and even more preferably, for four to fourteen weeks.

Preferably, after a period of administration of the phosphoaminolipid extract, the therapy is discontinued for four to 52 weeks and restarted. Even more preferred, the therapy is restarted after eight to fourteen weeks.

A preferred manner of administration of the phosphoaminolipid extract is 0.5–1.0 mg weekly for four to eight weeks and discontinued. Administration is restarted after a period of four to eight weeks. This cycle of administration and breaks is repeated as necessary.

The effective amount, 0.5–1.0 mg of phosphoaminolipid extract is usually administered in a solution suitable for subcuttaneous administration. A typical solution for administration contains 0.5 to 1.0 mg extract/ml with suitable preservatives, buffers and salts. The manner of administration may comprise intramuscular, subcutaneous, or intravenous injection, or by oral, rectal or transdermal delivery forms. A preferred route of administration is by subcutaneous injection.

Embodiments of the present invention provide clinical benefits to individuals infected with HIV. These benefits are highlighted in the Example which follows.

EXAMPLE 1

In this example, individuals diagnosed with HIV infection received a phosphoaminolipid extract purchased under the trademark "CANTASTIM™" (Cantacuzino Institute—Bucharest, Romania). HIV infection was established by the presence of anti-HIV antibodies by two EIA tests and confirmed by Western Blot procedures. Individuals exhibiting AIDS were identified as a sub-group of individuals which tested positive for HIV infection. Each individual received 0.5 mg of the phosphoaminolipid extract subcutaneously. This dose was repeated weekly for eighteen weeks. Blood samples were taken at two to three week intervals for thirty-two weeks.

FIG. 1 graphically describes the CD4 percent of patients receiving the phosphoaminolipid extract over time in weeks. As described in FIG. 1, the open rectangles are indicative of individuals with AIDS. The open circles are indicative of all HIV individuals, including those with AIDS. These data, with respect to all HIV patients, demonstrate an increase in CD4 percent in week 10, up to 20%. This increase was maintained over initial CD4 percent for over a six month period. At week 32 the CD4 percent had fallen only slightly to 19%.

With respect to AIDS patients, the data demonstrated a similar increase in CD4 percent in week 10. In week 10, the CD4 percent had increased from 13% to 16%. This increase was maintained for a 35 week interval. In week 32, the CD4 percent had fallen to only about 15%.

Figure 2:
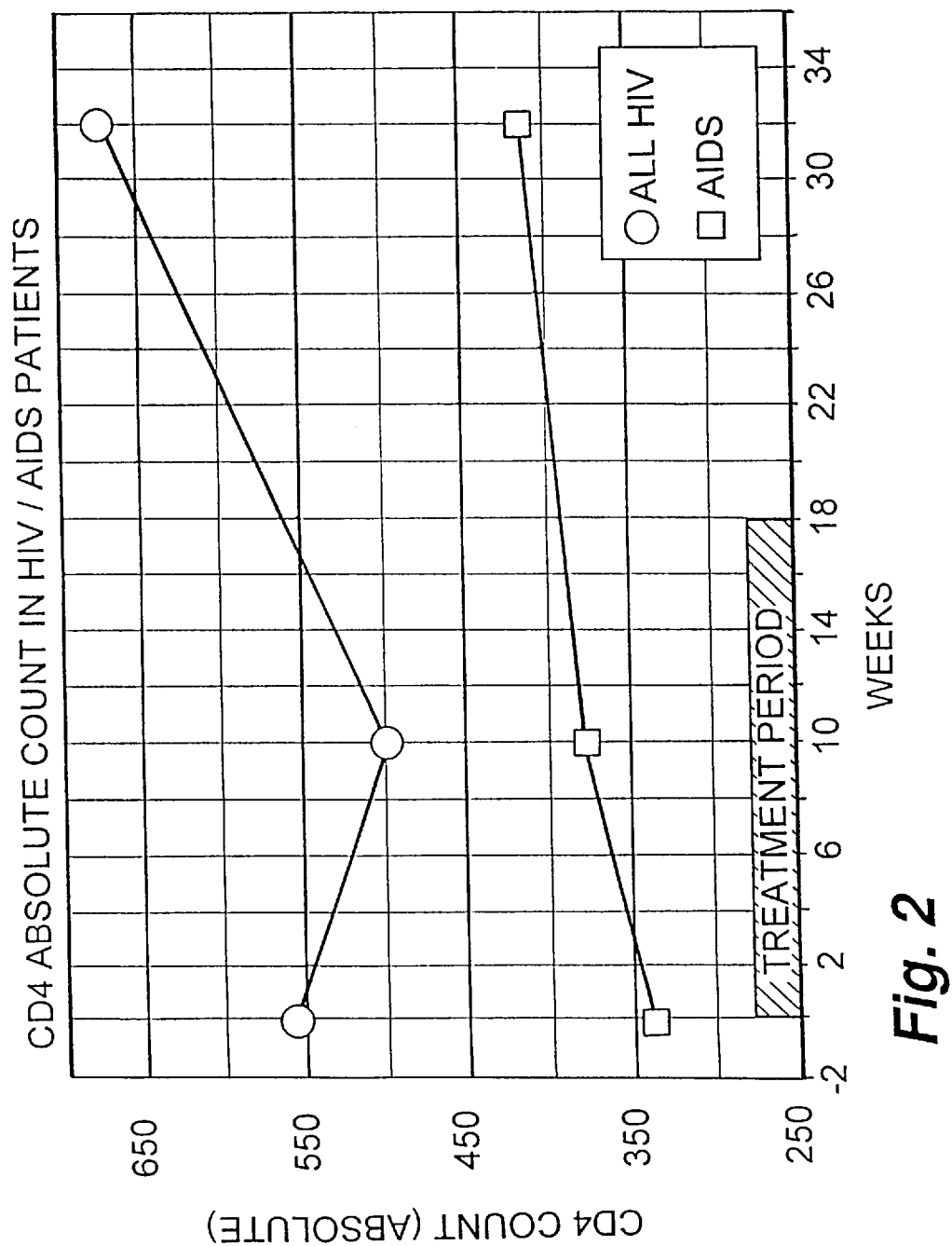
FIG. 2 graphically depicts CD4 absolute count in HIV/AIDS patients receiving treatment in accordance with the present invention.

FIG. 2 graphically illustrates CD4 absolute count in the same group of individuals over time in weeks. An open circle is indicative of all HIV infected individuals. An open rectangle is indicative of individuals exhibiting AIDS. These data indicate an increase in absolute CD4 count in HIV patients which remains elevated at week 32. These individuals collectively exhibit a CD4 absolute count upon initiation of the therapy of 550. This count dropped to 500 in week 10, but rose to 675 in week 32.

In individuals exhibiting AIDS, the data suggests an increase in absolute CD4 count. These individuals collectively exhibit a CD4 absolute count of less than 350. At week 10, the count had risen to almost 400, and by week 32, fourteen weeks after therapy had been discontinued, a count of over 400.

Figure 3:
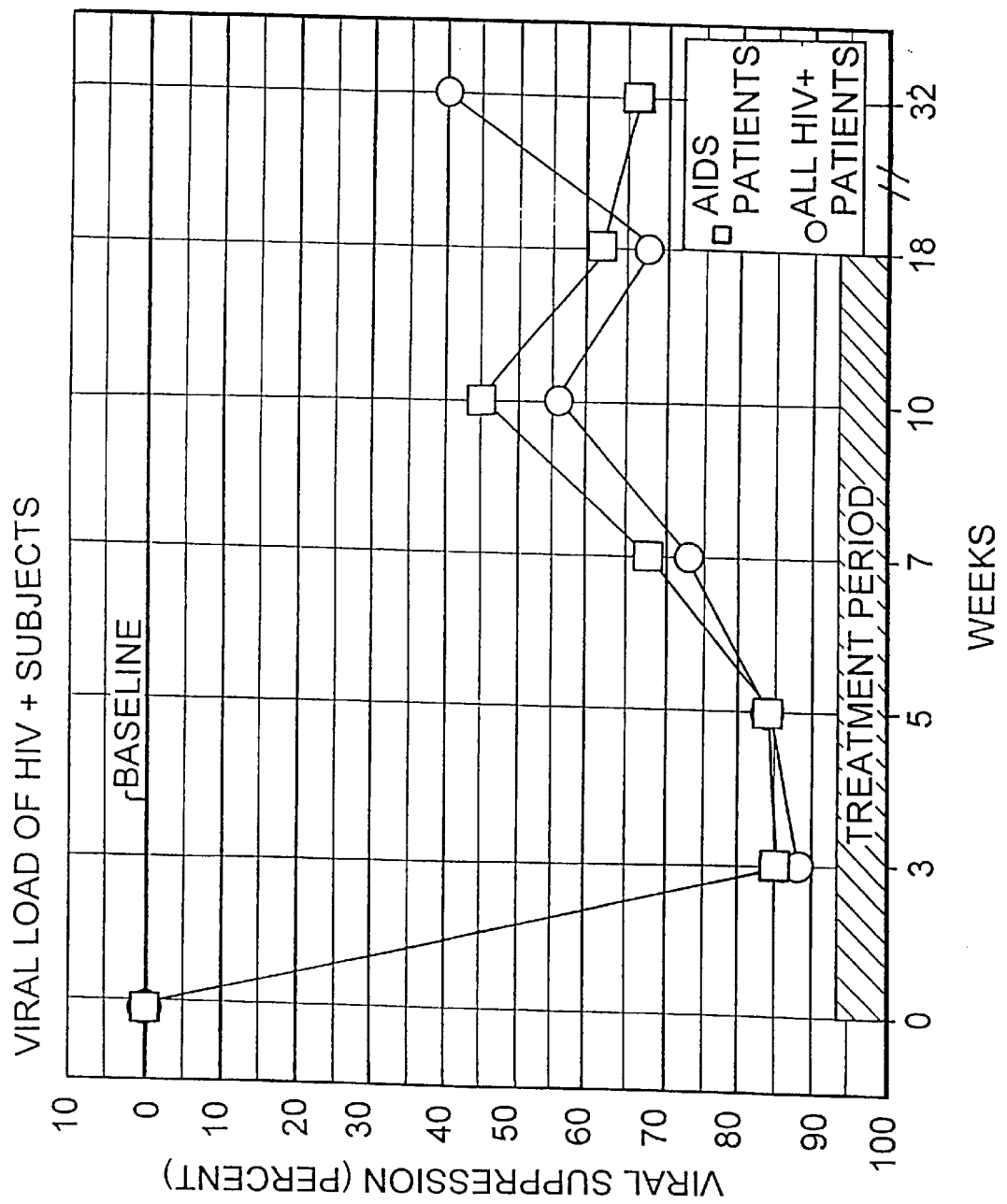
FIG. 3 graphically depicts viral load of HIV positive individuals receiving treatment in accordance with the present invention.

FIG. 3 graphically represents the viral load of individuals infected with HIV receiving treatment over time in weeks. Data is expressed as viral suppression as a percent of a baseline value established as therapy was initiated. Again, individuals with HIV infection are identified with open circles. Individuals exhibiting AIDS are identified with open rectangles. Typically, one would expect plasma viremia to follow the levels reported by Mr. Piatek et al., "High-levels of HIV-1 in Plasma During All States of Infection Determined by Competitive PCR", Science, 259, 749–54 (1993). These levels are set forth below in Table 1.

| Plasma Viremia and Clinical Stage | |
| --- | --- |
| Clinical Stage | Viremia (virus/ml) |
| Acute (primary) infection | $5 \times 10^6$ |
| Asymptomatic | $8 \times 10^4$ |
| Early symptomatic | $35 \times 10^4$ |
| AIDS | $2.5 \times 10^6$ |

The data of FIG. 3 indicates, for all individuals with HIV infection receiving treatment in accordance with the present invention, a marked reduction of the initial viral load by week 3. Those with HIV infection exhibit a reduction of 85%. A reduction was maintained through week 32, rising slowly during such period to a 40% reduction over the initial virus load.

Those with AIDS showed a similar reduction in week 3, of between 85–90%. This reduction rose to approximately a 45% reduction compared to the initial level before falling again to 65% reduction in week 32.

CLINICAL ENDPOINTS

Body Weight

The wasting syndrome, defined as the unintentional loss of more than 10% of body weight over a short period of time, is a devastating complication of AIDS. Weight loss in patients with HIV infection tends to be periodic, occurring particularly in relation to episodes of secondary infection or gastrointestinal disease.

Many factors are likely to be involved in the pathogenesis of weight loss in patients with HIV infection. For example, the intake of energy may be compromised by anorexia due to disease or the side-effects of drug treatment, by upper gastrointestinal disease, enteropathy, or by gastrointestinal infection that interferes with the absorption of nutrients and by a deranged intermediary metabolism.

Figure 4:
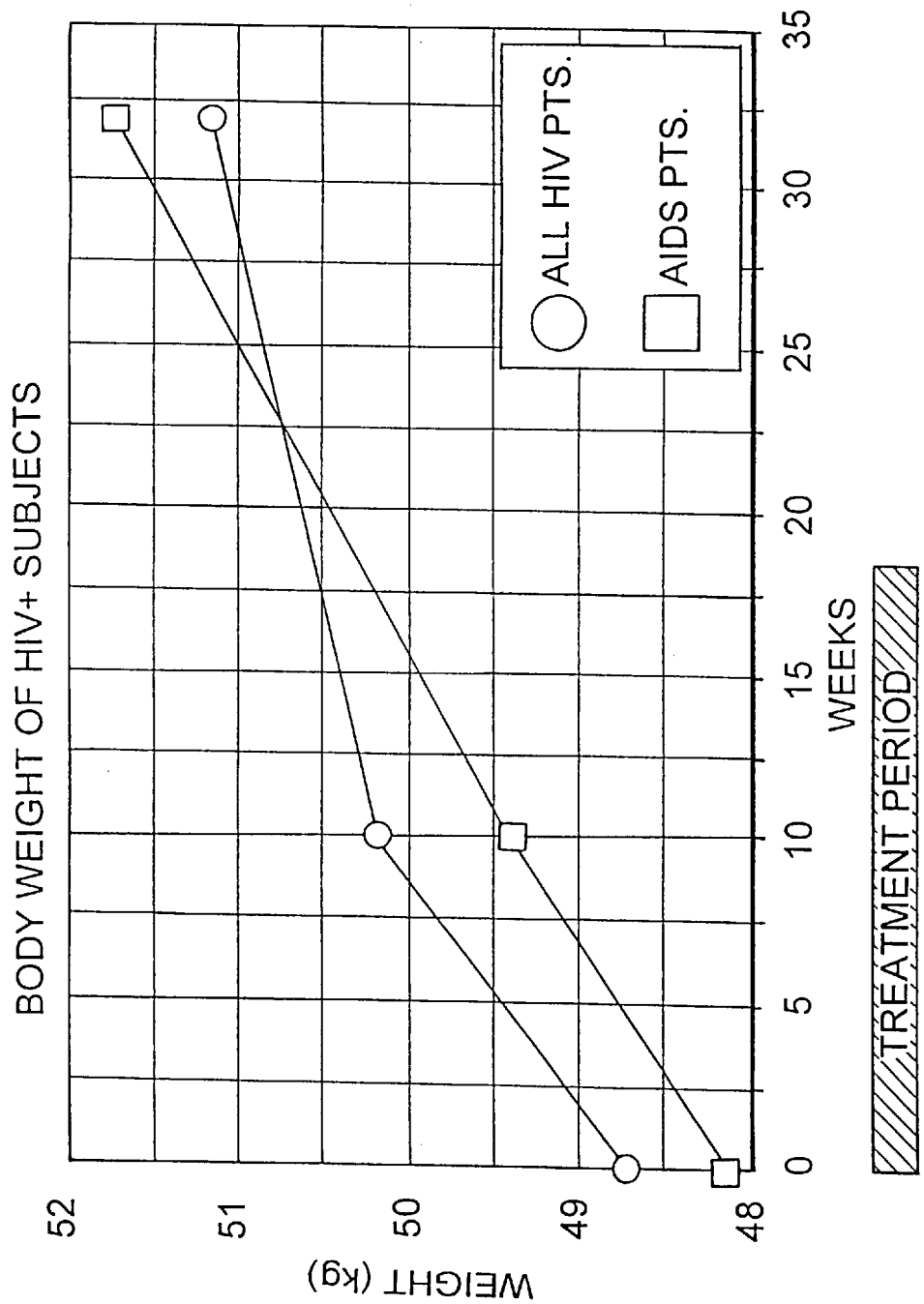
FIG. 4 graphically depicts body weight of HIV positive individuals receiving treatment in accordance with the present invention.

In this study, individuals exhibiting AIDS and receiving treatment did not lose, but actually gained body weight. FIG. 4 graphically depicts body weight over time of all HIV infected individuals and AIDS individuals over time in weeks. The body weight values represent averages of all subjects in each category. HIV infected individuals are indicated with open circles. Individuals exhibiting AIDS are indicated with open rectangles. Individuals exhibiting AIDS experienced body weight gain during the four months of treatment and which continued another three months after the treatment had been discontinued.

Average values for AIDS patients began at 48 kg at the initiation of therapy. At the 32 week point these patients had an average value of over 51.5 kg.

Similarly, average values for HIV positive patients were approximately 48.75 kg. upon initiation of therapy. At the 32 week point, these individuals collectively had an average value of 51 kg.

Response to Treatment for Opportunistic Infections

Three patients in the AIDS group entered the study with active pulmonary tuberculosis (TB). All three patients started anti-tuberculosis treatment five months before the study began but without clinical improvement. In normal situations, a TB patient experiences clinical improvement (no cough and no fever) after 3–4 weeks of the treatment initiation. Before the study was initiated (in the recruitment period), two patients with pulmonary tuberculosis also experienced a severe form of Herpes Zoster. After initiating the treatment, a good response was noticed to the anti-tuberculosis drugs and resolution of the Herpes Zoster condition. All three TB patients experienced a net clinical improvement of pulmonary tuberculosis disease in less than one month.

The patients with Herpes Zona Zoster did not receive any anti-viral treatment. However, improvement of the clinical symptoms were noticed two weeks after treatment.

One of the AIDS patients who suffered from pulmonary tuberculosis and Herpes Zona Zoster also experienced oral candidiasis, and another non-TB AIDS patient had persistent vaginal candidiasis prior to therapy. Both patients responded well to the local treatment for oral candidiasis and to both general and local treatment of vaginal candidiasis.

In the follow-up period of eight months, the AIDS patients experienced no recurrence of the existing and treated opportunistic infections. No clinical signs of pulmonary TB, Herpes Zona Zoster or candidiasis were noticed in the follow-up period.

Three AIDS patients in the period of recruitment were so sick that they were unable to work and were bedridden. After one month of treatment, these individuals+ condition improved such that they were able to work, and resumed a normal social life.

It will be seen from the foregoing example that the present method produces a stabilized or improvement in immune system function. This improvement is clinically manifested in an increase in body weight and response to therapy directed to opportunistic infections. It is manifested in the reduction in opportunistic infection. Most importantly, it is manifested in an improved quality of life. The present method is cost effective. The method of the present invention is affordable, in terms of industrial countries and developing countries.

Embodiments of the present invention are capable of modification and alteration which modifications and alterations are within the purview of the present invention as described in the following claims.

We claim:

1. A method of treating a subject infected with human immunodeficiency virus comprising:

administering to a subject infected with human immunodeficiency virus an immunomodulating phosphoaminolipid extract derived from bacteria of the genus *Psuedomonas aeruginosa* in an amount effective to cause at least one of the outcomes selected from the group consisting of:

(a) an increase in $CD4^+$ cells in the subject; and (b) a reduction in the levels of circulating human immunodeficiency virus in the subject.

2. The method of claim 1, wherein said immunomodulating phosphoaminolipid extract is an ethanol extract of *Pseudomonas aeruginosa* comprising 88–92% phospholipid and aminolipid, 3–5% sugar and 5–7% protein.

3. The method of claim 2 wherein said immunomodulating phosphoaminolipid is administered subcutaneously.

4. The method of claim 2 wherein said immunomodulating phosphoaminolipid is administered every day to every thirty days.

5. The method of claim 2 wherein said immunomodulating phosphoaminolipid is administered every five to fifteen days.

6. The method of claim 5 wherein said immunomodulating phosphoaminolipid is administered for up to 52 weeks.

7. The method of claim 5 wherein said immunomodulating phosphoaminolipid is administered for up to 32 weeks.

8. The method of claim 1 wherein said immunomodulating phosphoaminolipid is administered weekly for four to fourteen weeks.

9. The method of claim 2 wherein said effective amount is 0.1–1 mg. of said phosphoaminolipid extract.

10. The method of claim 2 wherein said effective amount is 0.5 mg. of said phosphoaminolipid extract.

11. The method of claim 6 wherein said administration of immunomodulating phosphoaminolipid is discontinued for periods of four to fifty-two weeks and resumed.

12. The method of claim 8 wherein said administration of immunomodulating phosphoaminolipid extract is discontinued for a period of eight to fourteen weeks and resumed.

13. A method for treating a subject infected with human immunodeficiency virus comprising:

administering to a subject in need of such treatment a *Pseudomonas aeruginosa* ethanol extract in an amount effective to increase $CD4^+$ cell count in the subject, wherein the extract is 88–92% phospholipid and aminolipid, 3–5% sugar and 5–7% protein.

14. A method for treating a subject infected with human immunodeficiency virus comprising:

administering to a subject in need of such treatment a *Pseudomonas aeruginosa* ethanol extract in an amount effective to reduce levels of circulating human immunodeficiency virus in the subject, wherein the extract is 88–92% phospholipid and aminolipid, 3–5% sugar and 5–7% protein.

15. A method for treating a subject infected with human immunodeficiency virus comprising:

administering to a subject in need of such treatment a *Pseudomonas aeruginosa* ethanol extract in an amount effective to prevent for a period of at least 10 weeks weight loss in the subject.

16. A method for treating a subject infected with human immunodeficiency virus comprising:

administering to a subject in need of such treatment a *Pseudomonas aeruginosa* ethanol extract in an amount effective to cause at least two of the outcomes selected from the group consisting of (a) an increase in $CD4^+$ cells in the subject;

(b) a reduction in the levels of circulating human immunodeficiency virus in the subject; and (c) prevention of weight loss for at least 10 weeks in the subject, wherein the extract is 88–92% phospholipid and aminolipid, 3–5% sugar and 5–7% protein.

* * * * *